(12) United States Patent
Neumann

(10) Patent No.: US 12,073,637 B1
(45) Date of Patent: Aug. 27, 2024

(54) APPARATUS AND METHOD FOR LOOP PLATING

(71) Applicant: KPN INNOVATIONS, LLC., Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 0 days.

(21) Appl. No.: 18/225,457

(22) Filed: Jul. 24, 2023

(51) Int. Cl.
| | |
|---|---|
| *G06K 9/00* | (2022.01) |
| *G06V 10/764* | (2022.01) |
| *G06V 20/68* | (2022.01) |
| *G16H 20/60* | (2018.01) |

(52) U.S. Cl.
CPC ............ *G06V 20/68* (2022.01); *G06V 10/764* (2022.01); *G16H 20/60* (2018.01)

(58) Field of Classification Search
CPC ........ G06V 20/68; G06V 20/20; G06V 10/58; G06V 20/52; G06V 10/50; G06V 10/764; G06V 2201/07; G06V 2201/08; G06V 10/143; G06V 10/145; G06V 10/25; G06V 10/44; G06V 10/462; G06V 10/56; G06V 10/811; G06V 10/82; G06V 20/653; G06V 30/142; G06V 30/153; G06V 10/774; G06V 40/20; G06V 40/23; G06V 10/141; G06V 10/245; G06V 30/10; G06V 40/161; G06V 20/62; G06V 20/63; G16H 20/60; G16H 40/63; G16H 10/60; G16H 40/67; G16H 50/20; G06T 2207/30128; G06T 2207/10024; G06T 7/0004; G06T 11/001; G06T 11/60; G06T 7/62; G06T 2207/10004; G06T 2207/10012

See application file for complete search history.

(56) References Cited

U.S. PATENT DOCUMENTS

| | | | |
|---|---|---|---|
| 2011/0182477 A1* | 7/2011 | Tamrakar | G06T 7/44 382/110 |
| 2019/0197289 A1* | 6/2019 | Codella | G06V 20/10 |

* cited by examiner

*Primary Examiner* — Alex Kok S Liew
(74) *Attorney, Agent, or Firm* — Caldwell Intellectual Property Law

(57) ABSTRACT

An apparatus and method for loop plating, the apparatus including a scanning system, at least a processor and a memory communicatively connected to the processor, the memory containing instructions configuring the processor to generate, using an optical scanning system, a first scan of a plate digitally connected to a user profile, track content data of the plate as function of the first scan, classify the content data to the user profile, wherein classifying the content data includes generating a loop assessment, verify the content data as function of the classification, generate, using the optical scanning system, a second scan of the plate, identify plating feedback as a function of the second scan, and update the user profile based on the plating feedback, wherein updating the user profile includes generating a progress report.

20 Claims, 4 Drawing Sheets

APPARATUS AND METHOD FOR LOOP PLATING

FIELD OF THE INVENTION

The present invention generally relates to the field of nutrition tracking. In particular, the present invention is directed to an apparatus and method for loop plating.

BACKGROUND

Current methods of meal preparation and delivery do not track the nutritional progress of a user. There is a need for a method of verifying that meals prepared and delivered to a user correlate to the nutritional needs of the user for nutritional tracking purposes.

SUMMARY OF THE DISCLOSURE

In an aspect, an apparatus for loop plating. The apparatus includes a scanning system wherein the scanning system includes an optical scanning system, at least a processor and a memory communicatively connected to the processor, the memory containing instructions configuring the processor to generate, using an optical scanning system, a first scan of a plate digitally connected to a user profile, track content data of the plate as function of the first scan, classify the content data to the user profile, wherein classifying the content data includes generating a loop assessment, verify the content data as function of the classification, generate, using the optical scanning system, a second scan of the plate, identify plating feedback as a function of the second scan, and update the user profile based on the plating feedback, wherein updating the user profile includes generating a progress report.

In another aspect, a method for loop plating. The method includes generating, using a scanning system including an optical scanning system, a first scan of a plate digitally connected to a user profile, tracking, by a computing device, content data of the plate as function of the first scan, classifying, by the computing device, the content data to the user profile, wherein classifying the content data includes generating a loop assessment, verifying, by the computing device, the content data as function of the classification, generating, using the optical scanning system, a second scan of the plate, identifying, by the computing device, plating feedback as a function of the second scan and updating, by the computing device, the user profile based on the plating feedback, wherein updating the user profile includes generating a progress report.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods loop plating. In an embodiment, loop plating may refer to a process of verifying a meal to be delivered to a user is the correct meal ordered. A delivery may include a delivery to a user's location or delivery to a user in a restaurant. Loop plating may include tracking the preparation and transposition of one or more meals to a user. Loop plating may include tracking and/or identifying a nutritional and physiological impact one or more meals has on a user's health. Loop plating may include continuously tracking and/or identifying a nutritional and physiological impact one or more meals has on a user's health of one or more users.

Aspects of the present disclosure can be used for the continuous tracking and accuracy of food and nutrients contained on a plate.

Aspects of the present disclosure can also be used to reduce trash and waste typically caused by disposable containers and incorrect fulfillment of meal orders.

Exemplary embodiments illustrating aspects of the present disclosure are described below in the context of several specific examples.

Figure 1:
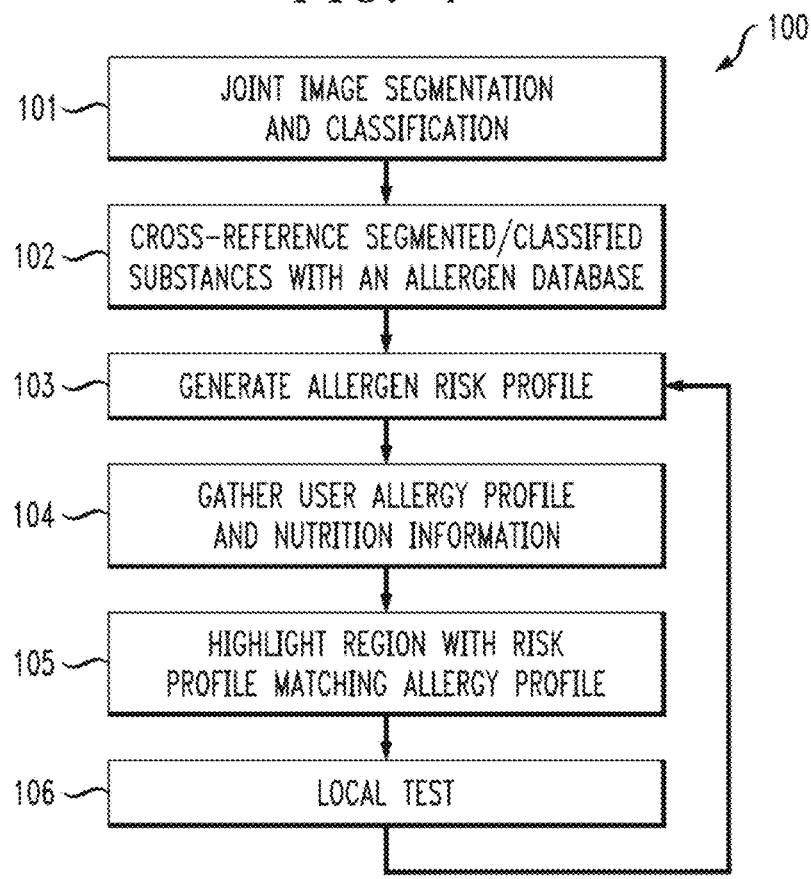
FIG. 1 is a block diagram of an exemplary embodiment of an apparatus for loop plating.

Referring now to FIG. 1, an exemplary embodiment of an apparatus 100 for loop plating is illustrated. Apparatus 100 includes a computing device 104, further including a processor 108. Processor 108 may include, without limitation, any processor described in this disclosure. Computing device 104 includes a memory 112 communicatively connected to the processor, memory 112 containing instructions configuring processor 108 to carry out the loop plating process. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to generate, using a scanning system 116, a first scan 120 of a plate 124 digitally connected to a user profile 128. Scanning system 116 may include an optical scanning system. A "scan," as used herein, is digital data of an object that has been captured through scanning. Digital data may refer to image data, features, symbols, models and like of an object as described through further below. Computing device 104 may generate a scan by scanning plate 124. "Scanning," as used herein, is the process of capturing data from an object using a sensor. For example, scanning plate 124 may include capturing a picture of plate 124. A "plate," as used herein, is an object used for serving an item. "Digitally connected," a used herein, refers to when a user profile and a plate are associated together by a digital system. As a non-limiting example, a user profile and a plate 124 may be digitally connected by way of an identification code 132. As a non-limiting examples, user profile 128 may be associated with the plate (or plate ID) in system database 140 to digitally connect them. A plate 124 may be composed of ceramic materials such as porcelain, bone china, plastic, wood, metal, and the like. Plate 124 may be composed of environmentally friendly material such as biodegradable or recyclable components in order to cut down on waste production, litter, and pollution. For example, environmentally friendly material may include material such as bamboo, palm leaf, sugar bagasse, wheat straw, bioplastics such as PLA (Polylactic Acid), stainless steel, and the like. Plate 124 may include a sealant/coating to prevent oxygen absorption by food and optimize the shelf life of food during transposition and storage, thus slowing down oxidation and spoilage. For example, plate 124 may be flash frozen for storage over a plurality of months. A sealant may include food-grade waxes, such as beeswax or paraffin wax; certain edible oils, like vegetable oil or mineral oil; silicone-based sealants; food-safe lacquers or coatings; food-safe polyurethane sealants, and the like.

A plate may include any container or item capable of serving, storing and transporting food. For example, a plate may include lids, containers of various shapes and sizes, cups, bowls, platters, trays, pans, and the like. In another example, plate 124 may include a serving plate, such as a rectangular serving platter for serving a turkey or ham at a holiday dinner. An "identification code (ID code)," as used herein, is a collection of words, letters, or signs used for identification purposes. Plate 124 may be labeled with an ID code 132 by way of a barcode or some other labeling method using radio-frequency identification (RFID), glyphs, universal product code (UPC), typed or handwritten text, QR code, and the like for the purposes of tracking and identifying plate 124. For example, RFID may include the use of electromagnetic fields to automatically identify and track a tag, such as a passive tag, attached or embedded into plate 124. In some embodiments, tag may include a passive tag. A "passive tag," as used herein, is a tag that uses the radio energy transmitted by a reader to transmit a signal. A tag may include a non-volatile memory to store data such as ID code 132, data from a user profile and other forms of data digitally connected to plate 124 as described further below. Scanning system 116 may act as an RFID reader and scan the tag to receive the information. A "user profile," as used herein, is a data structure containing information related to a user. User profile is described further below. In some embodiments, computing device 104 may receive an identification code 132 from the user profile 128. For example, a user may place an order with an alimentary provider, wherein the identification code 132 of a plate 124 may be digitally connected/attached to the order/user profile 128. An "alimentary provider," as used in this disclosure, is a person or entity that prepares alimentary products such as meals, food items, and/or drinks, including without limitation a restaurant, a food delivery service, or the like. The identification code 132 may be additionally associated with a meal order placed by a user. For example, an order for chicken wings and fries may be digitally connected to plate 124 by way of barcode. In some embodiments, user profile 128 may contain a plurality of ID codes 132 matched to a plurality of different plate 124 for one or more meal orders/requests by user. For example, a user may place one or more orders to an alimentary provider to prepare 30 different plates 124 for 30 different meals to be delivered to the user. In this example, the alimentary provider may be a meal preparation company, such as HelloFresh®, that prepares bulk/multiple meals to be delivered on a weekly or monthly basis.

Still referring to FIG. 1, computing device 104 may generate a first scan 120 to verify that the identification code 132 of the plate 124 matches the identification code 132 of the user profile 128. A first scan 120 may refer to a scan of plate 124 prior to user engagement. User engagement may refer to an interaction with a user and plate 124, such as delivery of plate 124 to user, consumption of food on plate 124, and the like. In some embodiments, scanning a plate 124 may include taking an image of plate 124 once food is placed onto it as described further below.

Still referring to FIG. 1, an "optical scanning system (OSS)," a used herein, is a computer input device that is configured to perform scanning using an optical method. A "scanning system," for the purposes of this disclosure, is a computer device that is configured to perform scanning. Optical scanning system may include handheld/portable scanners such as wand scanners, cordless scanners, handheld flatbed scanners, mobile scanners, pen scanners, and the like. Optical scanning system may include a camera. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object. In some cases, image data may be generated by a camera. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively where "image" is used as a verb, in this disclosure, it refers to generation and/or formation of an image.

Still referring to FIG. 1, in some embodiments, OSS 116 may include an optical character reader to identify the identification code 132 on plate 124. Optical character recognition or optical character reader (OCR) includes automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases. a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 5-8. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in in this disclosure.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, in some embodiments, apparatus 100 may include a machine vision system that includes at least a camera as described above. A machine vision system may use images from at least a camera, to make a determination about a scene, space, and/or object. In some cases a machine vision system may be used for world modeling or registration of objects within a space, which may be referred to a plate 124 model in this disclosure. For example, the machine vision system may be used to identify and track the placement of each item of plate 124. This identification may be used to register the quantity of each item on plate 124 using machine-learning processes as described further below. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and $\phi$ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

An exemplary machine vision camera that may be included in an environmental sensor is an OpenMV Cam H7 from OpenMV, LLC of Atlanta, Georgia, U.S.A. OpenMV Cam comprises a small, low power, microcontroller which allows execution of machine vision applications. OpenMV Cam comprises an ARM Cortex M7 processor and a 640× 480 image sensor operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detection motion, for example by way of frame differencing algorithms; marker detection, for example blob detection; object detection, for example face detection; eye tracking; person detection, for example by way of a trained machine learning model; camera motion detection, for example by way of optical flow detection; code (barcode) detection and decoding; image capture; and video recording.

Still referring to FIG. 1, user profile 128 may include a biological extraction. A "biological extraction" as used in this disclosure, includes any element of physiological state data. Physiological data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological data may be obtained from a physical sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like.

Continuing to refer to FIG. 1, biological extraction contains a plurality of user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides* vulgates', *Bacteroides-Prevotella*, Barnesiella species, *Bifidobacterium* longarm, *Bifidobacterium* species, Butyrivbrio crossotus, *Clostridium* species, Collinsella aerofaciens, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, Methanobrevibacter *smithii*, yeast minimum inhibitory concentration, bacteria minimum inhibitory concentration, yeast mycology, fungi mycology, Odoribacter species, Oxalobacter formigenes, parasitology, *Prevotella* species, Pseudoflavonifractor species, *Roseburia* species, Ruminococcus species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1.

Still referring to FIG. 1, in some embodiments, computing device 104 may retrieve user profile 128 from system database 140 using ID code 132, wherein ID code 132 is received from digital data of first scan 120. Additionally, ID code 132 may be received from an alimentary provider through a user interface, database, and the like. For example, computing device 104 may use a machine-learning process, such as a classifier, computational algorithm, and the like to sort and match an ID code 132 to an ID 132 of a user profile 128 of the plurality of user profiles 128 stored within system database 140.

Still referring to FIG. 1, user profile 128 may include a discovery center experience as disclosed in U.S. Nonprovisional application Ser. No. 18/099,346, filed on Jan. 20, 2023, and entitled "METHOD AND SYSTEM FOR PREDICTING ALIMENTARY ELEMENT ORDERING BASED ON BIOLOGICAL EXTRACTION," the entirety of which is incorporated herein by reference. A "discovery center experience" as used in this disclosure is defined as a set of simulated data generated at an online platform, known as a discovery center, which describes various potential health experiences to optimize a user's health. "Simulated data," as used in this disclosure is defined as taking a large amount of data and using it to mimic real-world scenarios of conditions. For example, a discovery center experience may include a future user experience wherein a comprehensive body scan may be performed, and user may be portrayed in a 3-dimensional version and have an experience to simulate what happens if user chooses optimal nourishment. A discovery center experience may also include one or a number of biological extractions from the user as described above. These biological extractions may include physical experiences, diagnostic testing, sleep patterns, fitness patterns, current nutrient levels or any other form of information coming from the user that is then utilized to determine their optimal nourishment needs. Nourishment needs include a complete state of physical, mental, nutritional, and spiritual wellbeing.

Still referring to FIG. 1, user profile 128 may include a set nutrient goal. A "set nutrient goal," as used herein, is a nutritional standard. A "nutritional standard," as used herein, is a nutritional need received from a user. A nutritional standard may be a type of diet such as keto, paleo, and the like. A nutritional standard may be the level of vitamins and minerals for consumption set by a user. The nutritional standard may include the level of fats, carbs, proteins, and the like for consumption set by a user. The set nutrient goal may be a nutritional standard tailored for a period time, for example, daily, monthly, annually, and the like. Computing device 104 may receive the user profile 128 through a graphical user interface (GUI), or system database 140 as described further below. A "graphical user interface," as used herein, is an interface configured to a allow an interaction between a user and a computer system. GUI may receive data from a user through a user input. A "user input," as used herein, is an interaction between a user and user interface, For example, user input may include, text submission, document upload, and the like. User input may be the submission of a set nutrient goal, physiological data, and the like.

Still referring to FIG. 1, computing device 104 is configured to track content data 136 of the plate 124 as function of the first scan 120. "Content data," as used herein, is information describing the contents of a plate 124. Content data may include intended items to be plated onto plate 124. Content data may include items plated onto plate 124. For example, content data 136 may describe the type of meal and ingredients plated onto plate 124. Content data 136 may include an image of plate 124 with the meals, ingredients plated, and the like. Content data 136 may include a model of plate 124 by a machine visions system. Content data 136 may be derived from image data captured by optical scanning system. Content data 136 may be derived from the ID code 132 of plate 124. Content data 136 may be received from a system database 140 communicatively connected to computing device 104. as a function of the ID code 132. A "system database," as used herein, is a data structure containing information related to the loop plating process. System database 140 may be used to receive and store user profile 128, image data, content data 136, plating history, alimentary provider data, and the like. Alimentary provider data may refer to information related to an alimentary provider, for example, the location, menu, and the like. Databases, as described throughout this disclosure, may be implemented, without limitation, as a relational database, a key-value retrieval database such as a NOSQL database, or any other format or structure for use as a database that a person skilled in the art would recognize as suitable upon review of the entirety of this disclosure. Databases may alternatively or additionally be implemented using a distributed data storage protocol and/or data structure, such as a distributed hash table or the like. Databases may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, system database 140 may include a plurality of tables. A "table," as used herein, is a categorization of data with a database. System database 140 may include a plating history table, a value report table, a durability guide table, a photobank table, a user profile table, and the like, each containing data as described in this disclosure.

Still referring to FIG. 1, in some embodiments, computing device 104 may be configured to receive a plating history of the plate 124 as function of the first scan 120. A "plating history," a used herein, is information related to preparing a plate. Preparations may include the cleaning, plating progress, and the like. The plating history may also include timestamps associated with each preparation. For example, a timestamp may be associated when the plate 124 was cleaned, plated with a first ingredient, second ingredient, fully plated, and the like. Plating history may also include the weight of plate 124 before an item is placed, and after each item/ingredient is plated. For example, plate 124 may be 4 oz, after plating the first ingredient, plate 124 may be 7 oz. In some embodiments, computing device 104 may infer the weight of each ingredient in the process of verifying the contents of plate 124 by performing mathematical calculations to derive the ingredient weight from the recorded weights of plate 124. For example, using the weights disclosed above, processor 108 may subtract 4 oz from 7 oz to derive that the first ingredient weighs 3 oz. Weights of ingredients and plate 124 may be used to verify correct serving sizes of a meal. Plating history may include shipping history, which may include identities, coordinates, addresses, or the like of locations at waypoints, depots, stops, and/or stations along a transport route and/or path, types of vehicles, particular vehicles, modes of transportation, conditions including temperature, degree of agitation, incidents, times of overall transport, storage along the route, transportation legs, or the like, and/or any other data concerning transport of a plate and/or contents associated therewith. Plating history may include storage history, which may describe durations, locations, types, and/or conditions of storage, such as without limitation shelf storage in a warehouse, frozen storage in a freezer or the like, refrigerated storage, storage in a cooler, and/or any other form of storage. Plating history may include preparation history, which may include any data concerning preparation of elements to be place on plates, including without limitation ingredients, dishes, recipes, procedures, or other data associated with preparation of consumables associated with a plate. Plating history may include consumption history, which may include any data concerning a history of consumption of meals and/or other consumables on plate, including without limitation a number of meals in which contents for a given usage were consumed, quantities or proportions consumed, quantities discarded, or the like. A plating history associated with ID code 132 may be received from an alimentary provider through a user interface or system database 140.

Still referring to FIG. 1, computing device 104 may be configured to receive a value report. A "value report," as used herein, is data structure containing information related to the nutritional value of an item. For example, the value report may describe the type, levels, and quantity of vitamins, minerals, protein, carbs, and the like a food item contains. In some embodiments, the value report may be for the collective meal on plate 124. For example, it may be the total nutritional value of meal containing seafood gumbo, turkey neck, and cornbread. In some embodiments, the value report may contain a report on a plurality of meals and/or food items. For example, the value report may report on each meal requested by a user in an order. A value report may be received from a alimentary provider through a user interface or system database 140. A value report may include data and/or be generated by computing device 104 using methods as disclosed in U.S. Nonprovisional application Ser. No. 16/888,303, filed on May 29, 2020, and entitled "METHODS AND SYSTEMS OF ALIMENTARY PROVISIONING," U.S. Nonprovisional application Ser. No. 16/531,318, filed on Aug. 5, 2019, and entitled "METHODS AND SYSTEMS FOR GENERATING A VIBRANT COMPATIBILITY PLAN USING ARTIFICIAL INTELLIGENCE," and U.S. Nonprovisional application Ser. No. 16/919,532, filed on Jul. 2, 2020, and entitled "METHODS AND SYSTEMS FOR CALCULATING NUTRITIONAL REQUIREMENTS IN A DISPLAY INTERFACE," each of which is entirely incorporated herein by reference.

Still referring to FIG. 1, computing device 104 may be configured to receive a durability guide. A "durability guide," as used herein, is a data structure containing information related to the shelf life of an item. The shelf life of a food item or meal may refer to the period during which the item retains an acceptable quality from a safety and organoleptic point of view. The durability guide may include information of the formulation, processing, packaging and storage conditions of a food item or meal. When food begins to spoil or age, it can lose important vitamins and minerals. For example, exposure to air, heat, and light can break down nutrients in food over time. The durability guide may include an assessment of potential nutritional value loss based on conditions such as time, storage conditions, and the like as described above. The durability guide may include information on one or more food items and/or meal related to a user as described above. A durability guide may be received from a alimentary provider through a user interface or system database 140.

Still referring to FIG. 1, system database 140 may include a photobank. A "photobank," as used herein, is a data structure containing a plurality of plate photos depicting meal options, ingredients, and menu options provided by one or more alimentary providers. For example, a plate 124 photo may include an image of a plate 124 with chicken, rice, and a broccoli side dish depicting the placement of each item on the plate 124. In some embodiments, plate 124 photos may include photos from optical scanning system. In some embodiments, system database 140 may be populated with plate 124 photos received from a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, computing device 104 may generate a web crawler to scrape plate 124 photos from a plurality of alimentary providers, cooking and/or farming based social media sites, websites, blogs, or forums. The web crawler may be seeded and/or trained with a reputable website, such as an alimentary provider's homepage, to begin the search. In some embodiments, computing device 104 may train a web crawler to retrieve and index photos of certain meal options, plating arrangements, and the like. For example, computing device 104 may train a web crawler to retrieve photos of a jelly donut that are not already indexed into system database 140. In another example, computing device 104 may train a web crawler to gather pictures of a certain grouping of meal options arranged onto a plate, such as a chicken pasta main dish, with a spinach side dish, and an apple pie dessert.

Still referring to FIG. 1, computing device 104 is configured to classify the content data 136 to the user profile 128. Computing device 104 may train a machine-learning model, such as a loop classifier 144 to classify content data 136, plating history, value report, durability guide and any other form of data described throughout this disclosure and output a loop assessment 148. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A "loop assessment," as used herein, is a data structure containing elements of data related to the loop plating process correlated to elements of a user profile 128. For example, ingredients plated on plate 124 may be correlated to a user's meal order in user profile 128. In another example, ingredients of content data 136 may be compared to a user's set nutrient goal, discovery center experience, physiological and the like for assessment purposes by computing device 104 as described further below. Computing device 104 may train loop classifier 144 with a loop training data set containing data correlating elements of content data 136 and plate 124 photos to a elements of a user profile 128. The loop training data set may contain data correlating elements of plating history, value report, content data 136, durability guide, and the like as described above to a meal request and other elements of a user profile 128. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training datai this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 is configured to verify the content data 136 as function of the classification, which may include using the loop assessment 148. Verification may refer to content data 136, such as the nutritional value of a meal on plate 124 matching or relating to a set nutrient goal of a user. Verification may refer to matching a meal request of a user. For example, user profile 128 may include a meal request containing instructions or requests for the type of food/nutrients to be plated onto plate 124 and delivered to the user. Computing device 104 may verify that the contents of plate 124 match the meal request. In some embodiments, this may include verifying that the serving size of each ingredient plated onto plate 124 correlates to the requested or desired serving size, diet, and/or meal of the user or alimentary provider. For example regarding a user, the user may request a keto based meal that is high-fat, adequate-protein, low-carbohydrate and is to be reflected in the serving sizes of the ingredients plated. Computing device 104 may use a machine-learning model or other computational methods as described herein to verify that the serving sizes of ingredients match the request of the user. Regarding an alimentary provider, computing device 104 may verify that the contents of plate 124 correlate to any recipes, instructions, or regulations the alimentary provider may have. For example, a regulation may be that any customer is only allowed to receive 5 oz of bread per order.

Still referring to FIG. 1, verification may refer to determining the impact a meal on plate 124 has on a user's physiological data. An impact may be positive, neutral, or negative. For example, a positive impact may be that meal on plate 124 corrects or improves an iron deficiency of a user. A neutral impact may be that meal on plate 124 just meets the daily value of recommended amounts of nutrients a person is to consume in a day. A negative impact may be that a meal on a plate 124 raises or worsen a user's cholesterol levels. In some embodiments, determining an impact may be based on the simulated data of the discovery center experience as described above. In some embodiments, computing device 104 may verify content data 136 by processing the loop assessment 148 to identify categories such as the set nutrient goal, meal request contents, and the like are meet. Determining an impact may include methods as disclosed in U.S. Nonprovisional application Ser. No. 17/007,227, and entitled "METHODS AND SYSTEMS FOR CALCULATING AN EDIBLE SCORE IN A DISPLAY INTERFACE," the entirety of which is incorporated herein by reference.

Still referring to FIG. 1, verifying the content data 136 may include computing device 104 comparing the plate 124 model generated using the machine vision system from to a plate 124 photo received from system database 140 corresponding to the meal order. A "plate model," as used herein, is digital data informing on the placement of an object within a space. For example, a plate model may be a registration of the placement of each item on plate 124 in regard to size, color, texture, and the like of each item. In another example, for a meal order by a user to an elementary provider for pasta, green beans, and a cookie, computing device 104 may compare the plate 124 model from the first scan 120 of plate 124 to a photo of pasta, green beans, and a cookie (a meal option provided by the alimentary provider) from the system database 140. In light of a mismatch or error in plating of plate 124, computing device 104 may generate and transmit a notification to an alimentary provider using a user interface or other form of electronic communication, such as email or text. A mismatch or error may refer to an item on plate 124 not corresponding to a meal request, incorrect portion sizes, and the like. Computing device 104 may use a photo classifier configured to classify the plate 124 model or plate 124 image data/photo to images corresponding to a user meal request. Meal request images may be received from the photobank in the system database 140. Photo classifier may receive plate 124 model and/or plate 124 image data/photo a inputs and output a photo assessment which may be used by computing device 104 to verify the contents of plate 124. A photo assessment, as use herein, is a data structure containing image data of the first scan 120 correlated to images related a meal request. For example, a photo of a plate, depicting a chicken salad, received from first scan 120 may be matched to a correlating photo of chicken salad stored in system, database 140. Photo classifier training data may correlate images in the photobank of the system database 140 to meal options, food items, and the like. Computing device 104 may determine, based on the photo assessment, and object or item in plate 124 model or plate 124 image not matched to a meal request to be an error in the plating process and send a notification to the alimentary provider for correction as described above.

Still referring to FIG. 1, in some embodiments, when contents of plate 124 cannot be verified, for instance because they are incorrect, missing, and the like, computing device 104 may generate and transmit a notification, such as an error message, to an alimentary provider or user. For example, computing device may transmit a message to a computing device or system communicatively connected to computing device 104 that alerts of an error and/or describes what and why contents of plate 124 cannot be verified. For example, computing device 104 may determine that plate 124 has 4 oz of fish when it is supposed to be 8 oz. A message may be sent to a device operated by the alimentary provider alerting of this error.

Still referring to FIG. 1, computing device 104 is configured to generate, using the scanning system 116, a second scan 152 of plate 124. Computing device 104 may generate the second scan 152 after user engagement. User engagement may refer to an interaction with a user and plate 124, such as delivery of plate 124 to user, consumption of food on plate 124, and the like. Generating second scan 152 after user engagement may refer to when plate 124 is being returned from a delivery. Computing device 104 is configured to identify plating feedback 156 as a function of the second scan 152. "Plating feedback," as used herein, is information relating to a plate 124 after user engagement. For example, plating feedback 156 may include photos or information describing/depicting ingredients or portions of meals not consumed by a user and left on plate 124. Computing device 104 may generate plating feedback 156 by taking a second photo of plate 124 upon rerun and/or generating a second plate 124 model using method as described above. Plating feedback 156 may include the return of plate 124. In some embodiments, computing device 104 may receive user feedback. "User feedback," as used herein, is information from a user received post user engagement. User feedback may be received by user input through GUI. User feedback may include comments by a user regarding the quality of the meal, delivery experience, time of consumption, and the like. User feedback may include a biological extraction or physiological data received after consumption of plate 124 contents and/or return of plate 124. Computing device 104 may digitally disconnect user profile 128 from ID code 132 upon receiving plating feedback 156. For the purposes of this disclosure, "digitally disconnecting" refers to the removal of the ID association between plate and user profile. For example, computing device 104 may update user profile 128 to remove or deactivate ID code 132. As a non-limiting example, computing device 104 may remove an association between plate (or plate ID) and user profile 128 in a database such as system database 140.

Still referring to FIG. 1, computing device 104 is configured to update the user profile 128 based on the plating feedback 156. An update may occur after return of plate 124. An update may occur continuously on a daily, weekly, monthly basis and the like. An update may refer to describing progress made with categories of user profile 128 and physiological data, such as a set nutrient goal. For example, a set nutrient goal may include a user consuming 50 grams of protein in a day, after return of plate 124, computing device 104 may determine a user has reached that daily goal and update the user profile 128 to reflect that. Computing device 104 may display and transmit any updates made through GUI. Computing may additionally update user profile 128 based on user feedback, plating feedback 156, loop assessment 148, value report, dietary guide and other forms of data as described through this disclosure.

Still referring to FIG. 1, updating user profile 128 may include generating a progress report 160. A "progress report," as used herein, is a data structure containing information related to changes in user's health after user engagement with a plate 124. A progress report 160 may include changes in the set nutrient goal as described above. A progress report 160 may include a nourishment score. A "nourishment score," as used in this disclosure, is data, including any character, symbolic, and/or numerical data, reflecting the current overall nutritional state of a user. A nourishment score may be transient and/or dynamic. A nourishment score may be graded on a continuum, where a score of zero may indicate a user who is in extremely poor nutritional health while a score of 100 may indicate a user who is in excellent nutritional health. A nourishment score may be calculated from one or more factors/categories that may be stored within user profile 128 or received through GUI containing items such as food intake, water intake, supplement intake, prescription medication intake, fitness practice, health goals, chronic health conditions, acute health conditions, spiritual wellness, meditation practice, stress levels, love/friendship status, purpose and values congruency, levels of joy and peace, gratitude mindset, body restoration coefficients, and the like. Computing device 104 may continuously generate and/or update progress report 160 based on plating feedback 156 received for each meal engaged in by the user. Determining nourishment score may include methods as disclosed in U.S. Nonprovisional application Ser. No. 17/007,227.

Still referring to FIG. 1, in some embodiments, computing device 104 may calculate the nourishment score by comparing the value report matched in the loop assessment 148 to data such as the gut-wall body measurement, nutrient body measurement, and the like from user profile 128 received as user feedback. For example, the value report of the loop assessment 148 may describe that meal to contain high levels of iron, computing device 104 may receive the user feedback and determine that the user's iron deficiency level have lowered after user engagement with plate 124.

Still referring to FIG. 1, progress report 160 may include a nutrient loss assessment. A "nutrient loss assessment," as used herein, is an assessment of nutrients lost during user engagement based on the time of consumption. For example, a meal delivered to the user may have contained 450 mg of calcium but based on the time of consumption a user may have only consumed 200 mg of calcium because off the shelf-life of the meal. Computing device 104 may calculate the nutrient loss of one or more meals using a machine-learning process as described in the is disclosure based on the classified durability guide and value report of loop assessment 148 compared to the time of consumption and other elements of data derived from plating feedback 156 and user feedback. In some embodiment, computing device 104 may adjust the nutrient needs or nutrient goals in user profile 128 based on the nutrient lost assessment. In some embodiments, computing device 104 may display scores or trends in scores or assessments using graphics such as grids, graphs, charts, and the like.

Figure 2:
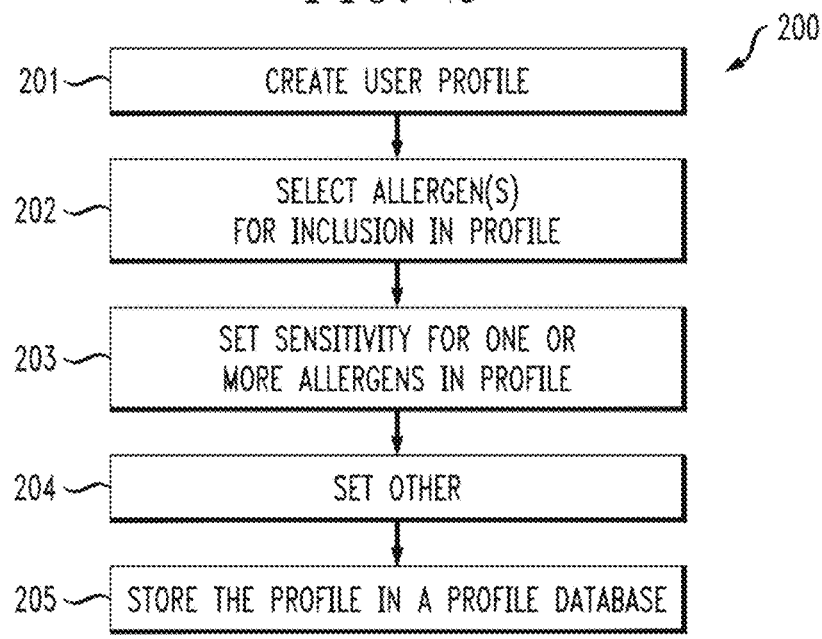
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, the use of a machine-learning model and process provides an improvement to the functioning of processor 108. For example, a machine-learning model, such as photo classifier, improves the performance power of processor 108 by classifying plate 124 model or plate 124 image data/photo to images corresponding to a user meal request to generate a photo assessment which may then be used by computing device 104 to verify the contents of plate 124. The quantity of data that goes into generating the photo assessment may vary and fluctuate based on a plurality of variables, such as the quantity and detail of meal requests received, along with the amount of meal request images received from the photobank in system database 140 that would be used in the classification process, and the like. Without the implementation of a machine-learning model, there would be a trade in the performance power of 108, such as time and accuracy, in order to sort the data and generate photo assessments that are then used in the verification process of content data 136 as described above. The ability to continuously train a machine-learning model cable of learning to identify new trends or correlations within a fluctuating quantity of data is a benefit that would not be realized otherwise, without the tradeoff in performance efficiency.

With continued reference to FIG. 2, computing device 104 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 2, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons, and used as described above. Accuracy score or another score as described above may indicate a degree of retraining needed for a machine-learning model such as a classifier; computing device 104 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative content data 136 to loop assessment 148.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to a cohort of user's having similar user body measurements such as food hypersensitivity. This may improve a machine learning training algorithm and model in generating, for example, nourishment scores and nourishment loss assessments by being able to more accurately identify correlations between user engagement with plate 124 and changes in user's health.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3A:
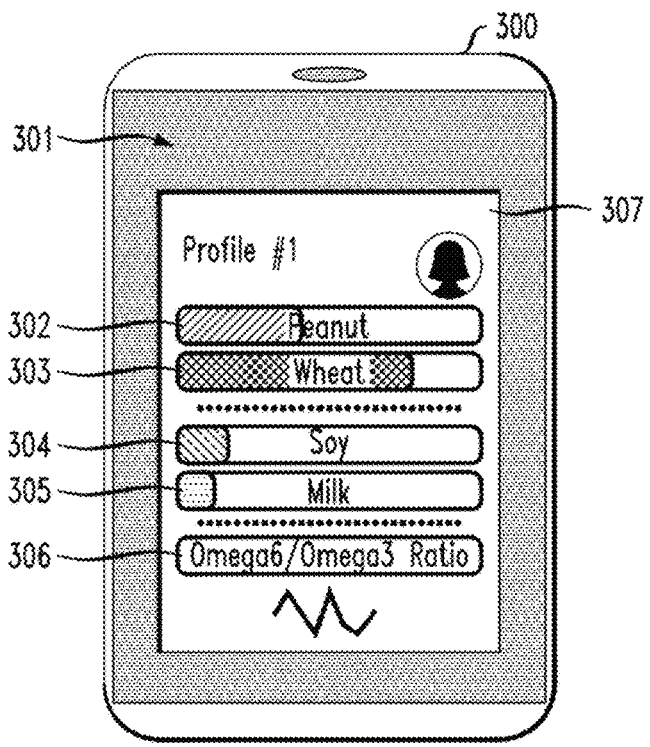
FIG. 3 is a diagram of an exemplary embodiment of neural network.
Figure 3B:
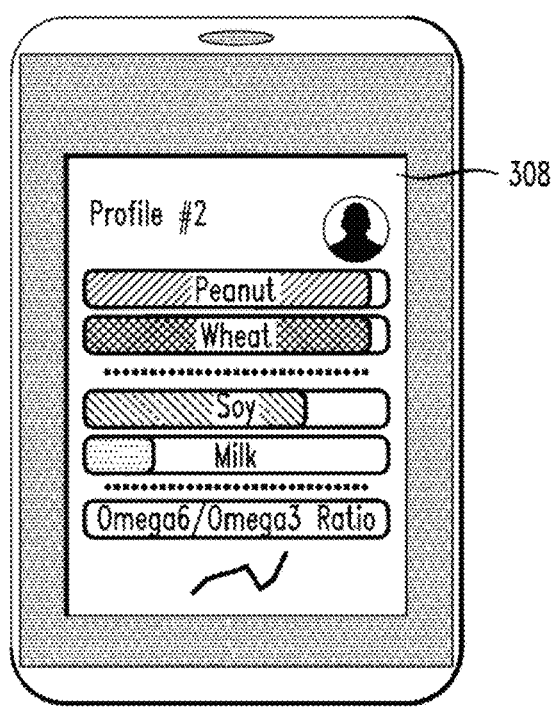

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 303, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
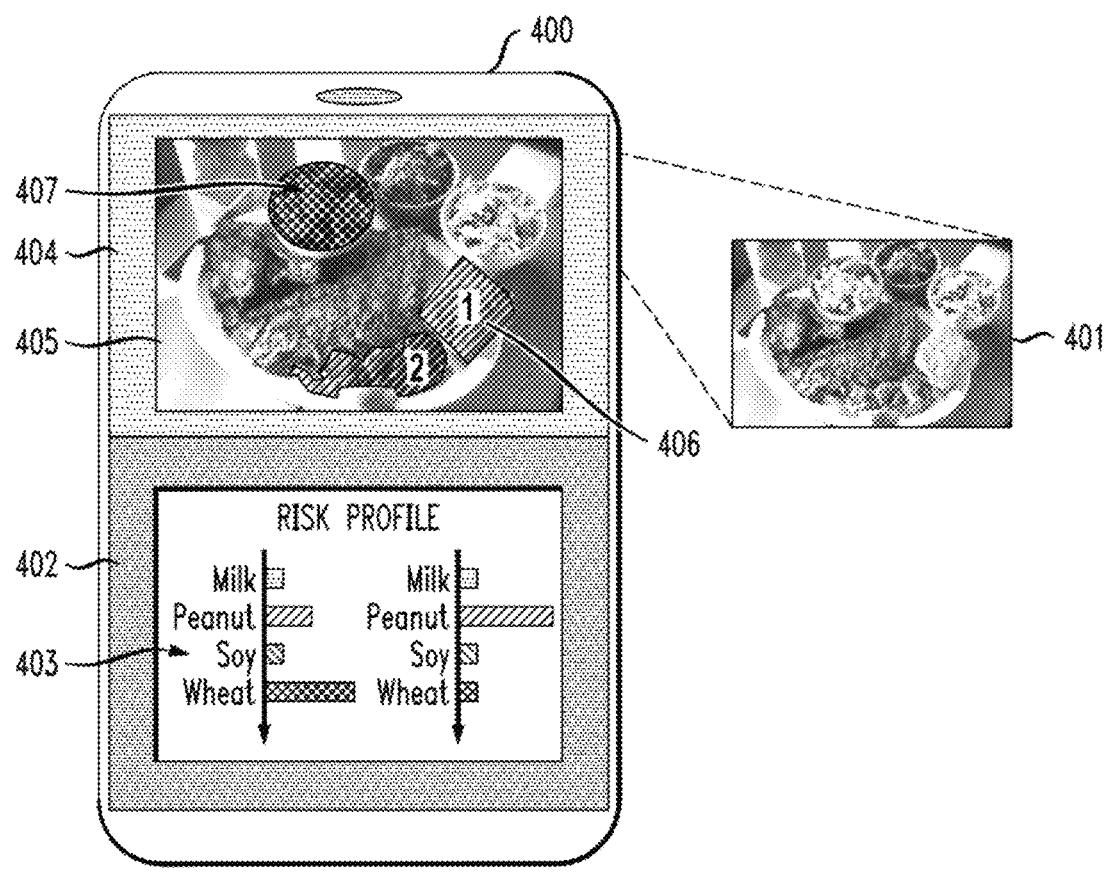
FIG. 4 is a diagram of an exemplary embodiment of a node of a neural network.

Referring now to FIG. 4, an exemplary embodiment of a node of a neural network is illustrated. A node may include, without limitation, a plurality of inputs x; that may receive numerical values from inputs to a neural network containing the node and/or from other nodes. Node may perform a weighted sum of inputs using weights w, that are multiplied by respective inputs xi. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight w, applied to an input x; may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights w, may be determined by training a neural network using training data, which may be performed using any suitable process as described above.

Figure 5:
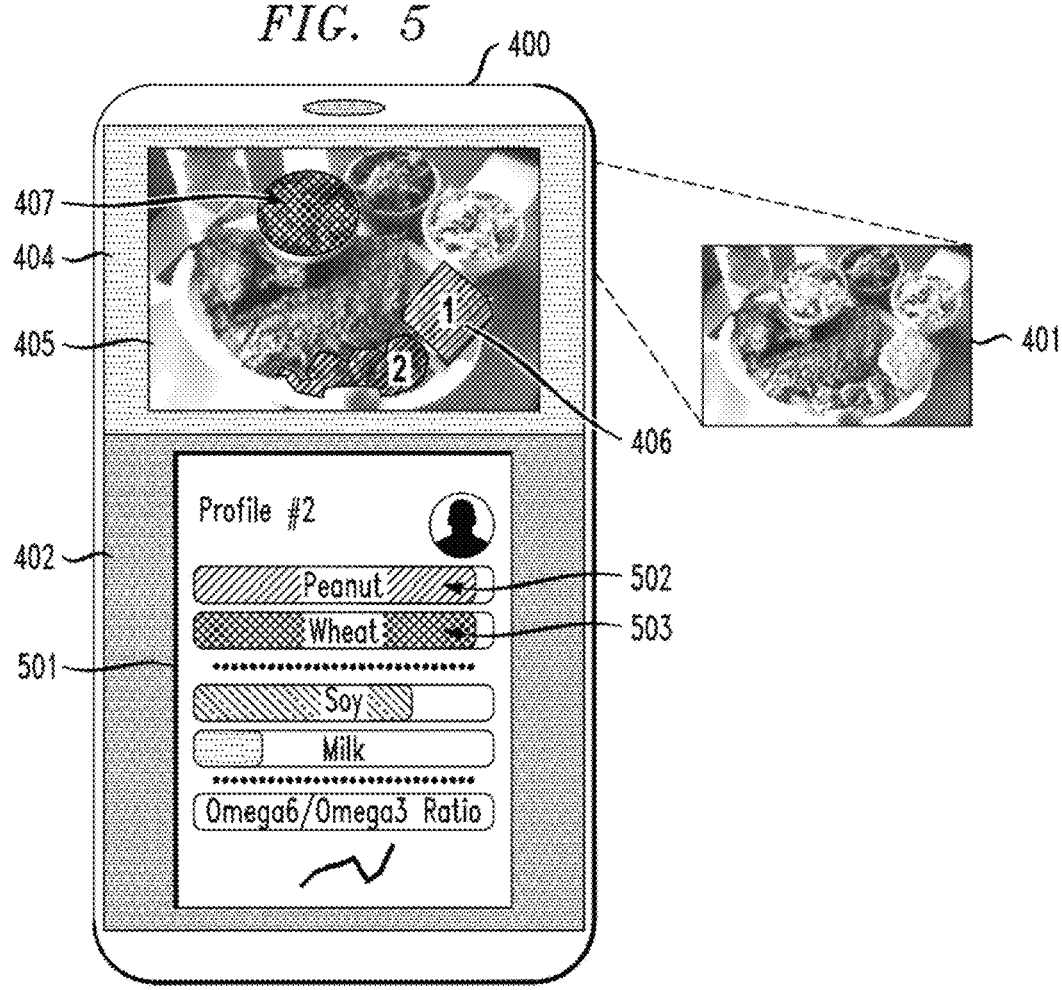
FIG. 5 is a flow diagram of an exemplary method for loop plating.

Referring now to FIG. 5, an exemplary flow chart of a method 500 for loop plating. At step 505, method 500 includes generating, using a scanning system, a first scan of a plate digitally connected to a user profile, for example, and as implemented in FIGS. 1-4. The optical scanning system may include a camera configured to capture an image of the plate as a function of the first scan. The optical scanning system may include an optical character reader configured to identify an ID code of the plate as a function of the first scan. The scanning system may include a machine-vision system configured to generate a plate model of the plate as a function of the first scan. The user profile may include physiological state data related to a user. The user profile may include a discovery center experience. The user profile may include a set nutrient goal related to a user. At step 510, method 500 includes tracking, by a computing device, content data of the plate as function of the first scan, for example, and as implemented in FIGS. 1-4. At step 515, method 500 includes classifying, by the computing device, the content data to the user profile, wherein classifying the content data includes generating a loop assessment, for example, and as implemented in FIGS. 1-4. Classifying the content data may include receiving a loop training data set containing data correlating elements of content data to elements of a user profile, training a machine-learning model using the loop training data set, and outputting, using the machine-learning model, the loop assessment. At step 520, method 500 includes verifying, by the computing device, the content data as function of the classification, for example, and as implemented in FIGS. 1-4. At step 525, method 500 includes generating, using the optical scanning system, a second scan of the plate, for example, and as implemented in FIGS. 1-4. At step 530, method 500 includes identifying, by the computing device, plating feedback as a function of the second scan, for example, and as implemented in FIGS. 1-4. At step 535, method 500 includes updating, by the computing device, the user profile based on the plating feedback, wherein updating the user profile may include generating a progress report, for example, and as implemented in FIGS. 1-4. The progress report may include a nourishment score. The progress report may include a nutrient loss assessment.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
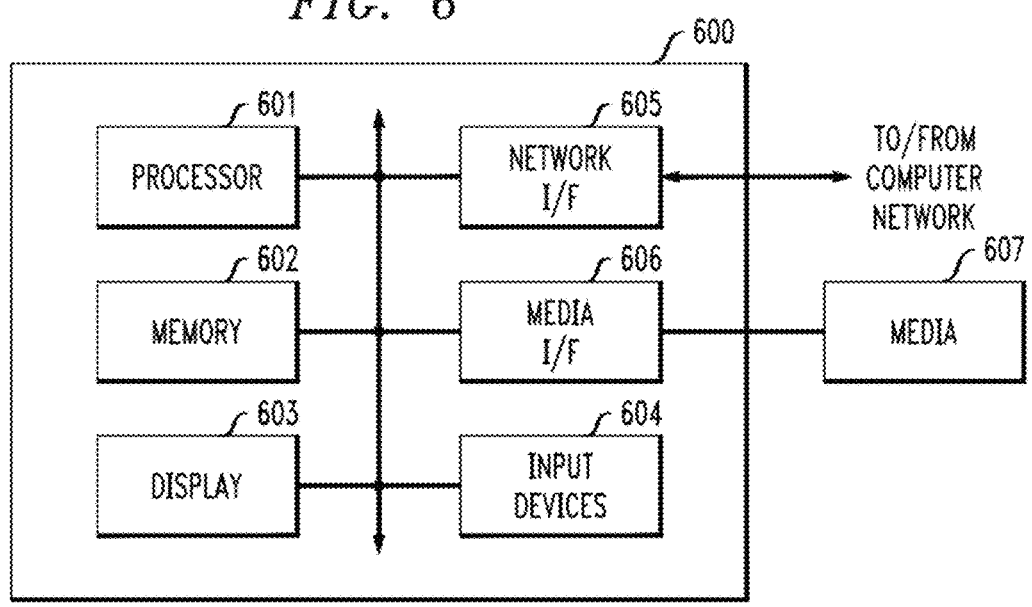
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatuses, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for loop plating, the apparatus comprising:
   a scanning system wherein the scanning system comprises an optical scanning system;
   at least a processor; and
   a memory communicatively connected to the processor, the memory containing instructions configuring the processor to:
      generate, using the scanning system, a first scan of a plate, wherein the plate is digitally connected to a user profile;
      track content data of the plate as function of the first scan;
      receive a value report for the content data, wherein the value report is a data structure containing information related to a nutritional value of the content data;
      classify the content data to the user profile, wherein classifying the content data comprises generating a loop assessment;
      verify the content data as function of the classification;
      generate, using the scanning system, a second scan of the plate;
      identify plating feedback as a function of the second scan; and
      update the user profile based on the plating feedback.

2. The apparatus of claim 1, wherein updating the user profile comprises generating a progress report.

3. The apparatus of claim 2, wherein the progress report comprises a nourishment score.

4. The apparatus of claim 2, wherein the progress report comprises a nutrient loss assessment.

5. The apparatus of claim 1, wherein the optical scanning system comprises a camera configured to capture an image of the plate as a function of the first scan.

6. The apparatus of claim 1, wherein the optical scanning system comprises an optical character reader configured to identify an identification code of the plate as a function of the first scan.

7. The apparatus of claim 1, wherein the optical scanning system comprises a machine-vision system configured to register items plated onto the plate.

8. The apparatus of claim 1, wherein verifying the content data further comprises verifying a serving size of an ingredient plated on onto the plate.

9. The apparatus of claim 1, wherein updating the user profile comprises updating a set nutrient goal on a continuous basis.

10. The apparatus of claim 1, wherein classifying the content data comprises:
   receiving a loop training data set containing data correlating elements of content data to elements of a user profile;
   training a machine-learning model using the loop training data set; and
   outputting, using the machine-learning model, the loop assessment.

11. A method for loop plating, the method comprising:
   generating, using a scanning system including an optical scanning system, a first scan of a plate digitally connected to a user profile;
   tracking, by at least a processor, content data of the plate as function of the first scan;
   receiving, by at least a processor, a value report for the content data, wherein the value report is a data structure containing information related to a nutritional value of the content data;
   classifying, by the at least a processor, the content data to the user profile, wherein
      classifying the content data comprises generating a loop assessment;
   verifying, by the at least a processor, the content data as function of the classification;
   generating, using the scanning system, a second scan of the plate;
   identifying, by the at least a processor, plating feedback as a function of the second scan; and
   updating, by the at least a processor, the user profile based on the plating feedback.

12. The method of claim 11, wherein updating the user profile comprises generating a progress report.

13. The method of claim 12, wherein the progress report comprises a nourishment score.

14. The method of claim 12, wherein the progress report comprises a nutrient loss assessment.

15. The method of claim 11, wherein generating the first scan comprises using a camera of the optical scanning system to capture an image of the plate as a function of the first scan.

16. The method of claim 11, wherein generating a first scan comprises using an optical character reader of the optical scanning system to identify an ID code of the plate as a function of the first scan.

17. The method of claim 11, wherein generating a first scan comprises using a machine-vision system of the optical scanning system to register items plated onto the plate.

18. The method of claim 11, wherein verifying the content data further comprises verifying a serving size of an ingredient plated on onto the plate.

19. The method of claim 11, wherein updating the user profile comprises updating a set nutrient goal on a continuous basis.

20. The method of claim 11, wherein classifying the content data comprises:
   receiving a loop training data set containing data correlating elements of content data to elements of a user profile;
   training a machine-learning model using the loop training data set; and
   outputting, using the machine-learning model, the loop assessment.

* * * * *